United States Patent [19]
Hersh

[11] Patent Number: 6,011,067
[45] Date of Patent: *Jan. 4, 2000

[54] ANTIOXIDANT COMPOSITION FOR THE TREATMENT OF PSORIASIS AND RELATED DISEASES

[75] Inventor: Theodore Hersh, Atlanta, Ga.

[73] Assignee: Thione International, Inc., Atlanta, Ga.

[ * ] Notice: This patent is subject to a terminal disclaimer.

[21] Appl. No.: 09/329,849

[22] Filed: Jun. 11, 1999

[51] Int. Cl.⁷ .................................................. A61K 31/195
[52] U.S. Cl. ......................... 514/562; 514/562; 514/627; 514/162; 514/165; 514/171; 514/474; 424/702; 424/439; 424/440; 424/441; 424/464; 424/54; 424/49; 604/58
[58] Field of Search ..................... 514/562, 561, 514/627, 162, 165; 424/439, 440, 54

[56] References Cited

U.S. PATENT DOCUMENTS

| | | | |
|---|---|---|---|
| 5,827,886 | 10/1998 | Hersh | 514/562 |
| 5,829,449 | 11/1998 | Hersh et al. | 131/202 |
| 5,906,811 | 5/1999 | Hersh | 424/54 |
| 5,922,346 | 7/1999 | Hersh | 424/439 |

FOREIGN PATENT DOCUMENTS 9505852  3/1995  WIPO .

*Primary Examiner*—Keith D. MacMillan
*Assistant Examiner*—Vickie Kim
*Attorney, Agent, or Firm*—Malcolm B. Wittenberg

[57] ABSTRACT

The present invention deals with the combination of several synergistic antioxidants including enzymatic co-factors as adjuncts to therapy of desquamating inflammatory disorders, such as psoriasis. These topical compositions are aimed to neutralize free radical species generated by such inflammatory conditions which are responsible for certain clinical signs and symptoms. As such, damage to skin causing destruction of elastin and collagen tissues is reduced. The present synergistic antioxidants may be combined with anti-inflammatories, including corticosteroids, antimicrobials, including zinc pyrithione, and other preparations useful in the therapy of desquamating disorders as psoriasis, seborrhoeic dermatitis and related skin and scalp conditions.

32 Claims, No Drawings

ANTIOXIDANT COMPOSITION FOR THE TREATMENT OF PSORIASIS AND RELATED DISEASES

TECHNICAL FIELD OF THE INVENTION

The present invention deals with the combination of several synergistic antioxidants including enzymatic co-factors as adjuncts to therapy of desquamating inflammatory disorders, such as psoriasis. These topical compositions are aimed to neutralize free radical species generated by such inflammatory conditions which are responsible for certain clinical signs and symptoms. As such, damage to skin causing destruction of elastin and collagen tissues is reduced. The present synergistic antioxidants may be combined with anti-inflammatories, including corticosteroids, anti-microbials, such as zinc pyrithione, and other preparations.

BACKGROUND OF THE INVENTION

The National Psoriasis Foundation estimates that there are more than six million Americans afflicted with psoriasis which is a chronic skin disorder. It is not contagious but its etiology is unknown. Most patients with psoriasis have several lesions confined to knees, elbows and scalp. Severe psoriasis affects larger areas such as the back, chest and legs and, not infrequently, the entire body. There are various types of psoriasis and thus there are a number of effective treatments or combinations, but not one that is specific or curative.

The therapeutic armamentariun used to combat the symptoms of psoriasis, available both by prescription and over the counter, include corticosteroids, coal tar, bath solutions, including salts from the dead sea, retinoids, vitamin D3, occlusion therapy, cyclosporine and methotrexate to name a few. Psoralens have been used with ultraviolet A radiation, despite its known carcinogenic properties, much like that caused by sun damage. Ultraviolet B radiation has also been used successfully in some cases.

Psoriasis is considered a hyperproliferative condition of the skin's epithelial cells. This dermatologic condition also includes seborrhoeic keratosis, eczema, warts and dandruff. Psoriasis may be a familial disease for which Bowcock and colleagues have disclosed a method for screening for psoriasis genetic susceptibility in U.S. Pat. No. 5,811,233 dated Sep. 22, 1998. Psoriasis, representing an uncontrolled proliferation of cells, has been variously treated with antiproliferative compounds such as retinoids directed at inhibiting these activities. In its normal state, TGF-Beta secretion has an inhibitory effect on epithelial cell proliferation. Piazza and Mazur disclosed the use of lysophosphatidic acid for treating hyperproliferative conditions in U.S. Pat. No. 5,565,439 issued Nov. 4, 1994. They claim that lysophosphatidic acid mimics the retinoids in their antiproliferative and TGF-Beta secretory properties. Their topical compositions included a variety of other agents with purported or hypothesized genetic properties influencing these hyperproliferative cutaneous maladies.

Various studies have shown increased enzyme activity in polymorphonuclear (PMN) leucocytes in the circulation of patients with psoriasis. Open and co-workers (Clin. Chine. ACTA 264:49, 1997) in Turkey correlated elastase levels in PMN leucocytes to disease activity. The PMN elastase levels were six-fold higher in psoriatic patients with active disease compared to controls, but only two-fold higher during quiescent stages of psoriasis. Not only is the elastase a sensitive marker of disease activity, it is also reflective of a concomitant inflammatory reaction which gives rise to free radical species. Elastase levels in PMNs also correlated with the total white blood cell (PMN) count and the levels of another reflector of inflammation, alpha-1-antitrypsin.

Psoriasis is characterized by hyper-proliferation and incomplete differentiation of epidermal keratinocytes. Psoralen plus ultraviolet A radiation (PUVA) represents one form of therapy, albeit there exists an increased risk of photocarcinogenesis with this treatment. Like the increased risk of cutaneous carcinomas and melanoma from UV radiation, oxygen and other free radical species may be pathogenetic of these neoplasias. PUVA leads to chromosome breakage through the formation of transferable clastogenic factors, whose genesis may be inhibited by the enzyme superoxide dismutase. Elastogenic factors have been detected in patients with psoriasis and with other illnesses associated with oxidative stress, where the free radical superoxide is produced both by phagocytes in the so-called "respiratory burst reaction" and from the process of lipid peroxidation. These elastogenic factors are present in the blood of psoriatic patients and are markedly increased during PUVA therapy. Thus, it is hypothesized by the present invention that the oxidative stress in psoriasis and especially during PUVA treatment may be ameliorated and the risk of photocarcinogenesis decreased by administration both of oral and topical antioxidants.

Psoralens, which are known to be mutagenic and carcinogenic, are components contained in many cosmetic preparations as aids to skin care. These photosensitizers may promote further skin reactions to ultraviolet radiation and result in permanent skin damage, cutaneous aging and malignancies even in patients with psoriasis.

Patients with psoriasis are often treated with oral methoxsalen (psoralens) and ultraviolet A radiation. This photochemotherapy, albeit effective, increases the risk of developing squamous cell skin cancer. Recent articles have also revealed an increased risk for malignant melanoma, especially among patients who receive over 250 treatments after 15 years since initiation. As noted hereinafter, the synergistic antioxidant complex of the present invention may be applied topically prior to and after UVA therapy to neutralize the free radicals so generated and thereby reduce the risk of development of cutaneous malignancies including melanomas in these patients.

Various novel therapies for psoriasis have recently been disclosed, albeit none address the issue of inflammation and free radicals ameliorated by the synergistic antioxidant complex of the present patent application. Quarles in U.S. Pat. No. 5,776,920 dated Jul. 7, 1998, teaches a preparation of salicylic acid, lactic acid, and urea in a moisturizing medium useful as topicals for psoriatic lesions applied once daily for four days. Braiman, using his own psoriasis affected skin, teaches the use of isomers of retinoic acid, namely II-cis-retinoic acid, as a therapeutic agent in U.S. Pat. No. 5,719,195 dated Feb. 17, 1998. Braiman teaches synthesis of neotretinoin as well as a way to irradiate a gel with retinoic acid to create this therapeutic isomer. Winkler and co-workers in U.S. Pat. No. 5,648,373 dated Jul. 15, 1997 teach the use of enzyme inhibitors to block the production of inflammatory mediators (the arachidonic acid cascade). These inhibitory compounds together with co-enzyme A-independent transacylase are purportedly useful in a variety of allergic and inflammatory disorders. Furthermore, the use of omeprazole in the therapy of these skin maladies is disclosed by Hasselkuss in U.S. Pat. No. 5,714,505 dated Feb. 3, 1998. U.S. Pat. No. 5,565,542 dated Oct. 15, 1996 by Eitan and collaborators teach the use of xanthine derivatives, namely, pentoxifylline, propentofylline and torbarylline, as topicals for psoriasis and atopic dermatitis. Medford teaches in U.S. Pat. No. 5,783,596 dated Jul. 21, 1998 the use of dithiolarxy-lates, especially dithiocarbamates as therapies for inflammatory diseases by blocking the induced expression of the endothelial cell surface adhesion molecule VCAM-1 and is thus also of value in treating atherosclerosis and related complications.

Psoralens and UVA bath therapy reportedly benefited the skin of eight of ten patients with psoriasis. Vallat and co-workers at the Rockefeller University (*J EXPT MED* 180:283, 1994) showed that PUVA bath therapy suppressed both immunological responses and epidermal activation in psoriasis by 70%. The pathologic increase of insulin-like growth factor receptors was reduced as was the increase in keratinocyte proteins at an abnormal site. They concluded this treatment reverses epidermal and lymphocytic activation and renders a more sustained remission in psoriasis.

It has been shown that patients with moderate or severe psoriasis have low blood selenium levels. Corrocher and co-workers (Clin. Chim. ACTA 179:121,1989) not only noted low serum selenium levels in patients with psoriasis but there was also a concomitant increase in the production of malondialdehyde, a reflector of free radical damage in the body. Harvima and collaborators in Finland, (ACTA Derm Venerol 73:88, 1993) supplemented such psoriasis patients with oral selenomethionine, although by this route neither skin selenium levels nor the clinical condition were affected. There was a distinct increase in the numbers of CD4-T lymphocytes which are able to modulate local immunologic mechanisms.

Burke and colleagues (Photoderm, Photoimmuno 9:52, 1992) have demonstrated in both human subjects and experimental animals that topical selenomethionine reduces the degree of UV irradiated damage to the skin. In the murine species, topical selenium also inhibited skin carcinogenesis. It is proposed by the present invention that free radical species are implicated in inducing these skin pathologies, thus, selenomethionine administered topically with its synergistic antioxidant partners will benefit patients with psoriasis, particularly those undergoing PUVA treatments, as preventive of skin cancers and reparative of skin damage.

Bruzzese et al. in U.S. Pat. No. 5,472,705 (Dec. 5, 1995) disclosed topical compositions of Omega 3 polyunsaturated acids for therapy of morbid affections like psoriasis. They included an alkyl ester of a triethylcitrate and a phenolic antioxidant. More recently, Jacob disclosed the use of ingredients of a latex extracted from the leaves of the *Wrightia tinctoria* R Br plant plus urea and polyethylene glycol as an herbal medication for psoriasis in U.S. Pat. No. 5,858,372, dated Jan. 12, 1999, which is herein incorporated by reference.

Cavazza et al. in U.S. Pat. No. 6,627,212 (May 12, 1997) which is herein also incorporated by reference, disclosed the use of esters of I-carnitine combined with hydroxy acids to treat dermatoses. A list of preferred hydroxy acids was further disclosed. The dermatoses listed as suitable for therapy with I-carnitine and these acids included ichthyosis, psoriasis and those induced by defective keratinization such as dandruff, acne, and palmar and plantar hyperkeratosis. Although the inventors recite these combinations, alone, or with accepted therapies for these dermatoses, no scientific evidence is given as to mechanisms by which they exert their pharmacologic effects.

The epidermis in psoriatic skin, much like skin which has sustained a significant burn, has increased levels of the enzyme xanthine oxidase. This enzyme, like phagocytic cells and skin fibroblasts, is capable of generating free oxygen radicals. In an experimental mouse model, an inflammation induced by a specific chemical (TAP) was associated with high xanthine oxidase activity and concomitant epidermal cell hyperplasia. This experimental finding is similar to what occurs in psoriatic skin, where there is an observed five-fold increase in xanthine oxidase and cellular hyperproliferation. It is not known if this increase in xanthine oxidase is responsible for epidermal hyperplasia in psoriasis.

A relationship has been established between the lesions of seborrhoeic dermatitis and pityrosporum yeast species. Although the numbers of *P. ovale* organisms do not correlate with disease activity, these may relate to the hosts' abnormal immune responses, such as occurs in patients with AIDS for these patients are known to have high frequencies of both seborrhoeic dermatitis and psoriasis. Patients with AIDS tend to have low blood counts of CD4-T lymphocytes. Their disease activity and their survival rate, however, depends not just on CD4-T lymphocyte cell counts but more on their HIV viral load and on the cells' content of glutathione (GSH). The lower the GSH level in the T-lymphocyte, the greater the replication of the HIV virus and the poorer is the prognosis for that patient. HIV positive subjects may also have low levels of selenium and of other antioxidants thus impairing immunologic protection. Selenium restores CD4-T lymphocyte function to deal effectively with pityrosporum yeasts. While inflammation induced by these yeasts in the scalp is prevalent, this creates free radical species and requires the cells' antioxidant defense mechanisms to help improve the severity of the seborrhoeic dermatitis.

Another mechanism for inflammation is due to the content of lipase by pityrosporum species which can generate free fatty acids. These too create free radicals requiring the antioxidant response to neutralize and nullify their toxic effects on the scalp. Additional therapies for seborrhoeic dermatitis include antimycotic agents and drugs that reduce sebum excretion. Shampoos with zinc pyrithione are used as adjuncts to therapy of seborrhoeic dermatitis. The mechanism is from zinc's healing and antimicrobial properties.

Zinc pyrithione shampoos may be further enhanced by the group of synergistic antioxidants of the present application. The glutathione cycle would neutralize free radicals and thereby reduce the inflammatory reaction and also decrease the levels of the deleterious enzyme elastase. It is hypothesized that the addition of topical GSH with selenomethionine or other synergistic partners will improve local immunologic function and be therapeutically beneficial.

Patients with seborrhoeic dermatitis have been shown to have low plasma levels of vitamin E, selenium, erythrocyte glutathione peroxidase, wherein selenium is a co-factor, and of polyunsaturated fatty acids. These low nutrient blood levels were recorded whether these patients with seborrhoeic dermatitis were HIV positive or HIV negative. These investigators ascribed these deficiencies to the pathogenesis of seborrhoeic dermatitis. They then patented a reparative shampoo composition as adjuvant therapy consisting of selenium, methionine and vitamin E as a protective response to scalp damage caused by the process of lipid peroxidation in these cases. See Ippolito, U.S. Pat. No. 5,290,809. Another composition of selenium as the sulfide is a well known component in anti-dandruff shampoos (Rappaport, M J., Int. Med. Res. 9:152, 1981). Bergbrant (Curr. Topics Med. Myco. 6:95, 1995) stresses that the numbers of the pathogenetic pityrosporum yeasts in seborrhoeic dermatitis patients is not related to their numbers in the scalps of affected individuals. The reference describes these microorganisms as etiologic due to altered cell-mediated immunity, akin to the low levels of CD4-T lymphocytes which are also glutathione depleted in patients with AIDS. The *Pityrosporum ovale* species, which is rich in lipase content, causes an inflammatory response in the scalp. There is then an increase in the release of the enzyme elastase from leukocytes which further generates free radicals and induces tissue damage. Impaired immune function, the inflammatory leukocytic reaction, and *P. ovale* lipase activity need be reduced to ameliorate seborrhoeic dermatitis. The antioxidant complex of the present invention is prime as an adjunct of therapy.

Drugs that reduce sebum and antimycotic therapies, including the anti-infective zinc pyrithione, require adjuvant therapy as from locally administered antioxidants, including glutathione, cysteine, superoxide dismutase and selenium. The antioxidants of the present invention neutralize the free radicals and ameliorate the inflammatory reaction which help to improve immune function although the frequency of seborrhea reported in patients with AIDS suggests that an alternate etiology may also be at play. Passi and Ippolito in Italy have reported deficiencies in blood levels of vitamin E, polyunsaturated fatty acids and erythrocyte glutathione peroxidase in patients with seborrhoeic dermatitis. These were at the same levels with HIV positive and negative patients compared to suitable controls. Further, Passi and Ippolito disclosed methods for adjuvant treatment of seborrhoeic dermatitis in U.S. Pat. No. 5,290,809 (issued Mar. 1, 1994). The disclosed composition contains pharmaceutical quantities of amino acid methionine, tocopherol and selenium.

Zinc pyrithione shampoos were evaluated in 32 subjects who suffered from dandruff, using half of the head for the test material and the other for a placebo (vehicle shampoo minus the zinc compound). Dandruff gradings and scalp biopsies were done. There was a progressive reduction in dandruff in the side of the head treated with the zinc shampoo. (Marks, R. et al. BRJ Derm. 1 12:415, 1985).

U.S. Pat. No. 4,503,047, showed the value of sulphur amino acids, like cysteine and methionine, in compositions for stimulating keratin formation in hair bulbs employing horseradish and mustard seed extracts. This invention related to hair growth stimulating compositions.

In other studies in human subjects, topical selenomethionine was investigated for its ability to reduce the degree of acute damage to the skin by sunburn as induced experimentally by ultraviolet irradiation. Eight women were treated for two weeks with a lotion vehicle and then with three concentrations of selenomethionine (0.002%, 0.02% and 0.05%). The researchers found that topical selenomethione was effective in protecting against acute UV damage to the skin, as measured by the minimal erythema dose, using a multiport solar ultraviolet simulator. Plasma levels of selenium in these volunteers remained unchanged, suggesting the protective effect of the selenomethionine was locally at the skin. The effects demonstrated by the topically applied selenomethionine in human volunteers suggests that the protection to ultraviolet irradiation is not simply a sunscreen effect. The selenomethionine is absorbed percutaneously and acts locally as a free radical scavenger.

Antioxidants, generally, have been found to inhibit all stages of carcinogenesis whereas some antioxidants are more specific and thus more effective against tumor imitation, or tumor promotion. Glutathione and selenium have been shown to play prime roles in protection of carcinogenesis, the latter particular in skin tumors, when selenium is applied locally but also in preventing other cancers, when selenium is taken orally and thereby replenishing selenium body stores. Likewise, glutathione, the most abundant tissue thiol and antioxidant, inhibits carcinogenesis. When glutathione concentration in cells is suppressed by chemicals so that glutathione levels are significantly lowered, chemical carcinogenesis is enhanced and progression of tumor numbers and tumor size increases. Thus, these studies show the value of glutathione in prevention of tumor formation, making it the ideal antioxidant ingredient along with other synergistically acting antioxidants included in these dermatologic preparations.

The role of intracellular GSH in irradiated cancer cells has been investigated. Reducing the intracellular levels of GSH in tumor cells increases their sensitivity to irradiation or oxidant damage mediated by activated neutrophils or macrophages. Inhibition of GSH synthesis also augments lysis of murine tumor cells by sulfhydryl-reactive anti-neoplastics. Thus, neoplastic cells depleted of their endogenous protective antioxidant, GSH, are more sensitive to radiation damage. Conversely, other studies have shown that increases in intracellular GSH are beneficial. Endothelial cells treated with an L-cysteine delivery agent not only enhance endothelial cell GSH concentration, but also protected these cells in an inverse, linear relationship from damage by endogenous hydrogen peroxide. This preventive role of GSH is of value in treating skin where the psoralens and UVA are being delivered.

Cysteine, one of the three amino acid constituents of GSH, has the "SH" group and thus, on its own, this thiol also possesses antioxidant properties. Therefore, it has been utilized as such or as a cysteine derivative, like n-acetyl-I-cysteine, for dermatologic, oral and prenatal preparations. It is the treatment of choice in hepatic toxicity by acetaminophen (Tylenol). Hildebrand, in U.S. Pat. No. 5,296,500 (Mar. 22, 1994), which is herein incorporated by reference discloses the use of N-acetyl-L-cysteine for regulating wrinkling of the skin, a sign of photoaging, and atrophy of the skin, also a sign of chronologic aging. The teaching is also both for prevention and treatment of sunburn and increasing the speed of skin pigmentation. Hildebrand also teaches its use in pharmacologically acceptable salts, including zinc compounds. His list of zinc salts does not list zinc pyrithione nor does this patent deal with therapy of dandruff, psoriasis, acne or other dermatoses.

Sharpe et al. in U.S. Pat. No. 5,637,616 (Jun. 10, 1997), which is herein incorporated by reference, taught the use of topical preparations with effective amounts of N-acetyl-L-cysteine in diseases mediated by proteases. These maladies include pemphigus, pemphigoid varieties and lichen planus.

However, none of the art considered above, taken either simply or in combination teach the use of reduced glutathione and a selenium source such as selenoamino acid for treating psoriasis, seborrheic dermatitis and related conditions.

SUMMARY OF THE INVENTION

The present invention is directed to a composition and method of treating psoriasis and related dermatological conditions such as seborrheic dermatitis. The composition comprises the combination of L-glutathione and selenium that acts as its synergistic co-partner, both incorporated in a suitable topical carrier.

DETAILED DESCRIPTION OF THE INVENTION

The dermatologics of this invention suggesting the use of the disclosed glutathione antioxidant synergistic group to represent a new adjunct to therapy of psoriasis and related diseases to combat free radical species created by the psoriatic inflammatory condition. The synergistic antioxidant complex plus related antioxidants may be combined with other topical ingredients with known beneficial effects such as anti-inflammatory agents, corticosteroids, or antimicrobials such as zinc pyrithione. Since free radical species increase the risks of developing cutaneous malignancies, particularly in psoriatics undergoing treatments with ultraviolet radiation, the glutathione antioxidant complex disclosed herein with its source of selenium such as selenomethionine, functionally acts as an anti-carcinogen. In addition, these compositions generally contain moisturizers as is known in the art of these therapeutics to help heal the dry, itchy, scaly, flaking lesions of psoriasis and seborrhea of the scalp.

The major functions of reduced glutathione (GSH) in protection against lipid peroxidation are related to three types of reactions, all inter-related and synergistic combining non-enzymic scavengers and enzymic and dietary provided antioxidants.

1. GSH with selenium co-factor glutathione peroxidases eliminate toxic peroxides.
2. GSH reduces oxidized forms of vitamin C which, in turn, maintains vitamin E in its reduced form promoting its metabolic functions. Thus, GSH supports the free radical reductions and free radical chain-terminating functions of the two nutrient antioxidants, vitamins C and E.
3. GSH functions through glutathione S-transferases to detoxify reactive aldehydes created during the process of lipid peroxidation.

As noted also, some cells have sodium dependent up-take systems for GSH, allowing cells to use both exogenous GSH and endogenously synthesized GSH, thereby enhancing a cell's ability to survive oxidative and free radical species damage. In this fashion, extra-cellular GSH also protects cells' survival. Investigative studies have shown that cells' viability correlates best with content of GSH in mitochondria. In the absence of GSH, lipid peroxidation is uncontrolled and leads to cell injury and death. Conversely, GSH protects cells from the ravages of free radicals, working synergistically with the antioxidant enzymes and the dietary vitamin antioxidants.

Without being bound to any particular theory, it is noted that reduced glutathione is employed in protecting cells and aerobic organisms against oxidative stress by itself being oxidized. Thus, L-glutathione must act in combination with other enzyme systems, like glutathione reductase, in order to be reduced so that it may renew its role as a free radical scavenger. GSH functions also coordinately with the enzyme glutathione peroxidase to break down hydrogen peroxide and lipid hydroperoxides. Glutathione peroxidase in the body requires selenium as a co-factor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxide in the presence of reduced glutathione. This reaction reduces glutathione to oxidized glutathione (GSSG). In turn, the GSSG is reduced back to GSH by the enzyme GSH reductase thereby maintaining abundant cellular GSH to scavenge free radicals anew. GSH reductase may be provided in these preparations through thiol rich yeast extracts, wheat germ extracts, both commercially available from various producers.

Further, glutathione and selenium act synergistically in vivo as they are both constituents of the same enzymatic system. GSH serves as a specific donor substrate while selenium, provided from alimentary sources or locally from topically applied preparations of selenoamino acids, selenium yeast extracts or selenoamino acid chelates, provides the prosthetic group of GSH peroxidase, during its synthesis. The glutathione and selenium antioxidant functions are intrinsically related since by keeping a peroxidase in action, the GSH and selenium, contribute to the removal of the dismutation product of free oxygen radicals, namely, hydrogen peroxide. In a broad sense, GSH and selenium modulate free radical chains initiated or sustained by hydro peroxides.

Selenium is used in the present invention for its role as an antioxidant as well as its anticarcinogenic and antimutagenic properties. Selenomethionine decomposes lipid peroxides and inhibits in vivo lipid peroxidation. Other selenoproteins also show a high degree of inhibition of lipid peroxidation in hepatic tissues of various species.

Compositions of reduced glutathione in the present invention comprise from about 0.001% to 15%, preferably from about 0.01% to 10%, more preferably from about 0.1% to 5% by weight.

As further noted from several of the examples which follow, the present invention further contemplates the use of additional optional expedients, such as superoxide dismutase (SOD). SOD is a ubiquitous cellular enzyme whose main function is in protecting cells against oxidative stress. Superoxide dismutases are a family of cytosolic metaloenzymes which specifically remove free oxygen radicals. There are three distinct forms of SOD, namely, CUZN SOD, MN SOD and extracellular SOD (EC-SOD) which is a copper enzyme. The differences in the SODs is in their amino acid sequence and their location at the active sites of the transition metals. It is hypothesized that the enzyme SOD, along with glutathione peroxidase and its selenium cofactor are effective preventative antioxidants because they eliminate molecules involved in the initiation of free radical reactions. SOD also protects intracellular reduced glutathione against free radical mediated chain oxidation as the combination of SOD and reduced glutathione prevents redox cycling reactions. It is noted that Kalopissis et al. in U.S. Pat. No. 4,129,644 (Oct. 10, 1975) disclosed the use of superoxide dismutases (SOD) for maintaining the keratinic structure of hair. SOD was also taught for protecting the skin from harmful effects of ultraviolet rays while also maintaining the skin's keratinic structure.

Vitamins, as those included in these preparations, are naturally derived from dietary fruits and vegetables, particularly ascorbates and carotenoids, but also are sources of tocopherols. Natural and synthetic vitamins may be taken orally as supplements in various foods and beverages or as pharmaceutic preparations of multivitamins and minerals. These dermatological preparations provide these vitamins in sufficient concentrations to exert locally their physiologic and pharmacologic properties.

Vitamin E, particularly in its alpha-tocopherol moiety, has been employed to inhibit oxidation of oils and fats in foods, cosmetic preparations and drugs. Vitamin E is not only an antioxidant but also has anti-inflammatory properties. In skin, vitamin E levels are present in dermis and epidermis, but are depleted by malnutrition and by ultraviolet light, thus their importance too in providing these to act in vivo as antioxidants, elevating the UV exposed tissue levels and thereby protecting affected skin cells. Vitamin E moisturizes and enhances skin smoothness. It is soothing and also participates in skin repair and wound healing, such as occurs in photoaging and sunburn and required in psoriasis treatments.

Cell membranes and plasma lipoproteins contain alpha tocopherol, which is a lipid soluble molecule that functions as a chain breaking (reparative) antioxidant. An—OH attached to the hydrophobic structure of tocopherol easily releases its hydrogen atom, so that peroxyl and alkoxyl free radicals generated during lipid peroxidation then may combine with this antioxidant instead of with adjacent fatty acid side chains, thereby terminating this chain reaction process of lipid peroxidation. Experimental evidence shows that the tocopherol radical migrates to the membrane surface. It is then reconverted to alpha tocopherol by its reaction with ascorbic acid (vitamin C). Thus, vitamins E and C are synergistic and minimize the toxic effects on lipid peroxidation in cell membranes and lipoproteins. Moreover, glutathione and selenium also act synergistically with vitamin E, the former, GSH, by regenerating alpha tocopherol from its tocopheroxyl radical form. Also, vitamin C and E, selenium and glutathione, in experimental animals, have been shown to work together as antioxidants in inhibiting skin tumor promotion and/or tumor progression.

Ascorbic acid, vitamin C, plays a significant role in skin metabolism and in synthesis of collagen as a co-factor in hydroxylation reactions for the formation and function of collagen. High vitamin C levels not only stimulate collagen but also reverse epidermal thinning and offer skin protection against ultraviolet rays. These properties of vitamin C are enhanced by using glucosamine where the polyamine complex protects the ascorbic acid, enhancing the antioxidant and anti-collagenase properties of these products. Vitamin C in protective liposomes or other micro-encapsulated lotion techniques may also be used.

Ascorbates can repair oxidizing radicals directly and are therefore characterized as chain-breaking antioxidants. Vitamin C, a water soluble exogenous small molecule antioxidant, is located in aqueous phases of cells while, as noted, vitamin E is in the lipid portion of membranes. Together they protect lipids and lipid structures against peroxidation. Vitamin C repairs the tocopheroxyl radical and permits that molecule to function again as a tocopherol free radical chain-breaking antioxidant. The ascorbate free radical produced in this reaction with tocopherol can be removed from the tissues by a dismutation reaction. The dehydroascorbate and the ascorbate radical can then be removed by enzyme systems that use NADH or NADPH as sources of reducing molecules and by GSH. Thereby, ascorbate is recycled to protect against the process of lipid peroxidation by its synergistic function with GSH and vitamin E.

Thus, these topical preparations will, in their preferred form, contain mixtures of vitamins C and E to enhance locally the antioxidant activities of the active ingredients, particularly in their function as chain-breaking antioxidants in lipid peroxidation, also for their photoprotective capacities. The additional compound, melanin, may also be included for its well-recognized antioxidant and photoprotective properties. All can be used in appropriate concentrations to provide UV radiation preventative and reparative properties in those patients with psoriasis also undergoing PUVA treatments.

Vitamins C and E not only work together as antioxidants in hydrophilic and hydrophobic areas of cells and cell membranes, but also work synergistically with reduced glutathione and the glutathione cascade, including selenium dependent glutathione peroxidase, and superoxide dismutase. Further beneficial pharmacologic effects are additive by using these in protective and enhancing encapsulating reservoir molecules, such as liposomes, nanospheres, glycospheres and others well known to those in the industry.

In a preferred embodiment, the compositions of the present application will be enhanced by the addition of zinc salts. Zinc may function by its healing properties as on wounds, particularly as zinc oxide, and also to render the present preparations odorless, presumably by removing traces of hydrogen sulfide, which could emanate from sulfur groups used in these preparations. Zinc may also be administered as one of the trace metals prepared in yeast extracts as mineral (zinc) glycopeptides. Compositions preferably comprise from about 0.001% to about 8% of a zinc salt, more preferably from about 0.01% to about 4%, more preferably still from about 0.1% to about 1.25%.

Zinc pyrithione has been used in a number of dermatologic preparations, including shampoos, sprays, creams and lotions. It is available in commercial preparations for management of dandruff, seborrhoeic dermatitis, flakes (as in psoriasis) and other skin maladies. Purportedly, this zinc salt possesses antibacterial and antifungal properties, particularly against pityrospora species present in seborrheic dermatitis scalps.

The medical literature has several reports of the beneficial use of zinc pyrithione alone in psoriatic patients. For example, U.S. Pat. No. 4,323,558 dated Apr. 5, 1982, teaches pharmaceutical compositions containing triethylenetetramine (Trien) for use in various inflammatory skin disorders. The inventor adds that Trien may be used in gels, ointments and lotions even with inclusion of zinc pyrithione with which Trien forms a clear solution of gel. U.S. Pat. No. 4,938,969 dated Jul. 3, 1990 teaches the use of non-toxic zinc salts in topical applications with ascorbic acid and tyrosine as a method for treatment of aging skin and photodamaged skin. The preferred range of use is 0.1 to 2.0 percent by weight. Other pyrithione salts have been disclosed such as sodium, magnesium, copper and chitosanpyrithione, with purported anti-bacterial and antifungal properties. The latter compound is disclosed in U.S. Pat. Nos. 5,015,632, 4,345,080 and 4,379,753, which are herein incorporated by reference, disclosing methods for preparing pyrithione crystals that yield the desired pearlescence in hair care compositions.

As an optional ingredient for inclusion in the present invention together with the synergistic antioxidant complex described above is the cytostatic agent zinc pyrithione and other agents and drugs useful in the management of these conditions, including seborrhoeic dermatitis and psoriasis. This composition may contain other cytostatic agents such as selenium sulfide, colchicine, coal tar, and others known in the industry. In addition, physiologically active steroid preparations may also be included such as hydrocortisone, cortisone, prednisone, beta methasone, clobetasol triamcinolone, dexamethasone, and others known in the art of these therapies. Other anti-inflammatories may also be added from the families of salicylates and the non-steroidals such as ibuprofen, indomethacin, and others also known in this pharmacology industry. Antibacterial, fungistatic and fungicidal agents may also be employed in this composition, depending on the intended therapeutic use, for example, specific anti-microbials may be added to the zinc pyrithione-antioxidant agents when treating the putative microorganism in seborrhoeic dermatitis, pityrosporum yeast species.

The active ingredients described above can be incorporated in any suitable pharmacologically acceptable carrier which is suitable for topical administration to the human skin. As such, the pharmacologically acceptable carrier must be of sufficient purity and have sufficiently low toxicity to render it suitable for administration to a human noting that the carrier can represent up to 99% but typically from at least approximately 80% of the total composition.

Typical compositions for use herein include a wide variety of physical forms. These include, but are not limited to, solutions, lotions, creams, oils, gels, sticks, sprays, ointments, balms, shampoo and pastes. Generally, such carrier systems can be described as being solutions, emulsions, gels, solids and aerosols.

Solvents are generally employed in the preparation of suitable topical compositions. Such solvents can either be aqueous or organic based and, in either case, the solvent must be capable of having dispersed or dissolved therein the above-described active components while not being irritating to the user. Water is a typical aqueous solvent while suitable organic solvents include propylene glycol, butylene glycol, polyethylene glycol, polypropylene glycol, glycerol, 1,2,4-butanetriol, sorbitol esters, 1,2, 6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is incorporated herein by reference.

Alternatively, the present composition can be formulated as a lotion containing from about 0.01% to 10% of the above described active ingredients. Further, the product can be formulated from a solution carrier system as a cream. A cream of the present invention would preferably comprise from about 0.1% to 15% and preferably from 1% to 5% of the above described active ingredients. Lotions and creams can be formulated as emulsions as well as solutions.

It is contemplated that as one embodiment, the active ingredients described above be used as a lotion or cream emulsion of the oil-in-water type or as a water-in-oil type, both of which being extremely well known in the cosmetic field. Multi-phase emulsions such as the water-in-oil type are disclosed in U.S. Pat. No. 4,254,105, the disclosure of which is incorporated herein by reference. The compositions may also be administered as a liquid, like in the different type of sprays available in this industry.

It is further contemplated that the active ingredients of the present invention be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 99% of an emollient plus to about 0.1% to 99% of a thickening agent. Reference is again made to U.S. Pat. No. 5,296,500 and the citations contained therein for a more complete disclosure of the various ointment, cream and lotion formulations for use herein.

It is important to supply locally both L-glutathione (in its reduced form) and synergistic antioxidants to restore epidermal glutathione levels and enhance the reparative antioxidant chain-breaking reactions. In addition to alleviating the psoriatic or other skin maladies, it becomes imperative to prevent UV ray damage to the affected skin by prophylaxis with skin care (sun protection) products for the prevention of free radical generation and their neutralization by locally applied antioxidant preparations, as proposed in the present application, particularly in patients undergoing PUVA treatments.

EXAMPLE 1

Cream

| | Ingredients | Percent |
|---|---|---|
| 1. | L-glutathione (reduced) | 0.20 |
| 2. | L-selenomethionine | 0.05 |
| 3. | N-acetyl-L-cysteine | 0.25 |
| 4. | A,C,E Liposome | 2.50 |
| 5. | Superoxide dismutase | 0.25 |
| 6. | Zinc pyrithione | 0.25 |

EXAMPLE 2

Spray

| | Ingredients | Percent |
|---|---|---|
| 1. | L-glutathione (reduced) | 0.20 |
| 2. | L-selenomethionine | 0.05 |
| 3. | N-acetyl-L-cysteine | 0.25 |
| 4. | A,C,E Liposome | 2.50 |
| 5. | Superoxide dismutase | 0.25 |
| 6. | Zinc pyrithione | 0.25 |

EXAMPLE 3

Shampoo

| | Ingredients | Percent |
|---|---|---|
| 1. | L-glutathioine (reduced) | 0.20 |
| 2. | L-selenomethionine | 0.025 |
| 3. | N-acetyl-L-cysteine | 0.25 |
| 4. | A,C,E Liposome | 2.00 |
| 5. | Superoxide dismutase | 0.10 |
| 6. | Dex-panthenol | 0.5 |
| 7. | Zinc pyrithione | 1.0 |

I claim:

1. A composition for treating psoriasis, seborrhoeic dermatitis and related skin and scalp conditions, said composition comprising as active ingredients L-glutathione and a source of selenium in a suitable carrier for topical application, said L-glutathione and selenium incorporated in said carrier in concentrations to reduce symptoms of psoriasis, seborrhoeic dermatitis and related skin and scalp conditions.

2. The composition of claim 1 wherein said source of selenium is a selenoamino acid.

3. The composition of claim 2 wherein said selenoamino acid is selenomethionine.

4. The composition of claim 1 further comprising zinc pyrithione.

5. The composition of claim 1 wherein said L-glutathione is present in an amount from approximately 0.001% to 15% (weight) based upon the weight of the composition.

6. The composition of claim 1 wherein said L-glutathione is present in an amount from approximately 0.01% to 10% (weight) based upon the weight of the composition.

7. The composition of claim 1 wherein said L-glutathione is present in an amount from approximately 0.1% to 5% (weight) based upon the weight of the composition.

8. The composition of claim 1 further comprising N-acetyl-L-cysteine.

9. The composition of claim 1 further comprising superoxide dismutase.

10. The composition of claim 1 further comprising vitamin E.

11. The composition of claim 1 further comprising vitamin C.

12. The composition of claim 1 wherein said active ingredients are encapsulated in protective membranes.

13. The composition of claim 1 wherein said protective membranes are selected from the group consisting of liposomes, nanospheres and glycospheres.

14. The composition of claim 1 further comprising a source of zinc.

15. The composition of claim 14 wherein said zinc is incorporated in said composition as zinc oxide.

16. The composition of claim 1 wherein said carrier is in the form of a member selected from the group consisting of a lotion, spray, ointment, cream, gel, emulsion and shampoo.

17. A method of treating human skin to reduce symptoms of psoriasis, seborrhoeic dermatitis and related skin and scalp conditions, said method comprising topically applying to human skin a composition comprising L-glutathione and a source of selenium in a suitable carrier in concentrations effective to reduce said symptoms of psoriasis, seborrhoeic dermatitis and related skin and scalp conditions.

18. The method of claim 17 wherein said source of selenium is a selenoamino acid.

19. The method of claim 18 wherein said selenoamino acid is selenomethionine.

20. The method of claim 17 further comprising zinc pyrithione.

21. The method of claim 17 wherein said L-glutathione is present in an amount from approximately 0.001% to 15% (weight) based upon the weight of the composition.

22. The method of claim 17 wherein said L-glutathione is present in an amount from approximately 0.01% to 10% (weight) based upon the weight of the composition.

23. The method of claim 17 wherein said L-glutathione is present in an amount from approximately 0.1% to 5% (weight) based upon the weight of the composition.

24. The method of claim 17 further comprising N-acetyl-L-cysteine.

25. The method of claim 17 further comprising superoxide dismutase.

26. The method of claim 17 further comprising vitamin E.

27. The method of claim 17 further comprising vitamin C.

28. The method of claim 17 wherein said active ingredients are encapsulated in protective membranes.

29. The method of claim 17 wherein said protective membranes are selected from the group consisting of liposomes, nanospheres and glycospheres.

30. The method of claim 17 further comprising a source of zinc.

31. The method of claim 16 wherein said zinc is incorporated in said composition as zinc oxide.

32. The method of claim 17 wherein said carrier is in the form of a member selected from the group consisting of a lotion, spray, ointment, cream, gel, emulsion and shampoo.

* * * * *